US010813679B2

(12) United States Patent
Lanois et al.

(10) Patent No.: US 10,813,679 B2
(45) Date of Patent: Oct. 27, 2020

(54) SURGICAL FASTENER MANIPULATION TOOL

(71) Applicant: Thomas Stuart Loftus, Johnson City, TX (US)

(72) Inventors: Daniel Brian Lanois, Frisco, TX (US); Thomas Stuart Loftus, Johnson City, TX (US)

(73) Assignee: Thomas Stuart Loftus, Johnson City, TX (US)

(*) Notice: Subject to any disclaimer, the term of this patent is extended or adjusted under 35 U.S.C. 154(b) by 125 days.

(21) Appl. No.: 16/208,652

(22) Filed: Dec. 4, 2018

(65) Prior Publication Data

US 2019/0290342 A1    Sep. 26, 2019

Related U.S. Application Data

(62) Division of application No. 15/927,266, filed on Mar. 21, 2018, now Pat. No. 10,595,917.

(51) Int. Cl.
*A61B 17/86* (2006.01)
*A61F 2/30* (2006.01)
*A61B 17/88* (2006.01)

(52) U.S. Cl.
CPC .......... *A61B 17/888* (2013.01); *A61B 17/863* (2013.01); *A61B 17/864* (2013.01); *A61B 17/8615* (2013.01); *A61F 2/30771* (2013.01); *A61F 2002/3092* (2013.01); *A61F 2002/3093* (2013.01); *A61F 2002/30622* (2013.01); *A61F 2002/30858* (2013.01); *A61F 2002/30995* (2013.01)

(58) Field of Classification Search
CPC .............. A61B 17/888; A61B 17/8615; A61B 17/8877
See application file for complete search history.

(56) References Cited

U.S. PATENT DOCUMENTS

2002/0169453 A1* 11/2002 Berger .................. A61B 17/60
606/295

* cited by examiner

*Primary Examiner* — Christian A Sevilla
(74) *Attorney, Agent, or Firm* — IVC Patent Agency; David O. Simmons (57) ABSTRACT

A surgical fastener manipulation tool in accordance with embodiment of the present invention is useful by a surgeon to place fasteners such as threaded screws. The surgical fastener manipulation tool selectively engages a mating structure of fastener for securing the fastener thereto. Thus, advantageously, the surgical fastener manipulation tool can be used for placing such fasteners and/or can be used for extracting (i.e., removing) such fasteners. The ability to extract a fastener (e.g., a threaded bone screw) with the same tool used for placing it is highly beneficial due to time savings during a surgical procedure and is advantageous with respect to prior art fastener manipulation tool configurations that require placement and extraction tools to be differently configured.

18 Claims, 7 Drawing Sheets

SURGICAL FASTENER MANIPULATION TOOL

CROSS REFERENCE TO RELATED APPLICATIONS

This divisional patent application claims priority from co-pending United States Non-Provisional patent application having Ser. No. 15/927,266 filed Mar. 21, 2018 entitled "Bone Screw And Tool For Use Therewith", which has a common applicant herewith and is being incorporated herein in its entirety by reference.

FIELD OF THE DISCLOSURE

The disclosures made herein relate generally to threaded fasteners and, more particularly, to bone screws and associated tools configured for use in surgical procedures.

BACKGROUND

It is well-known that there are various diagnoses for which it is needed or desired to hold bones within a human or animal body in a fixed position with respect to each other. One such diagnosis for which it is desired to hold bones within a human or animal body in a fixed position with respect to each other is an accidental or intentional fracture of a bone. Another such diagnosis for which it is desired to hold bones within a human or animal body in a fixed position with respect to each other is in a surgical fusion procedure (e.g., a sacroiliac fusion).

Irrespective of the diagnosis leading to the need or desire to hold bones within a human or animal body in a fixed position with respect to each other, one or more bone screws are well-known to be used for such purpose. The bone screws, which are often used in combination with other fastening implements (e.g., bone plates) can be threadedly inserted into the two or more separate bone pieces (e.g., two or more different bones and/or segments of a given bone) for securing such two or more separate bone pieces in fixed relationship with respect to each other. The bone screw(s) thereby hold(s) the bone pieces in a stationary position with respect to each other and, in some usages, thereby allows bone material to grow therebetween to fuse the bone pieces together. Such bone growth supplements the strength provided by the bone screw to prevent the bones pieces from moving with respect to each other.

Figure 1:
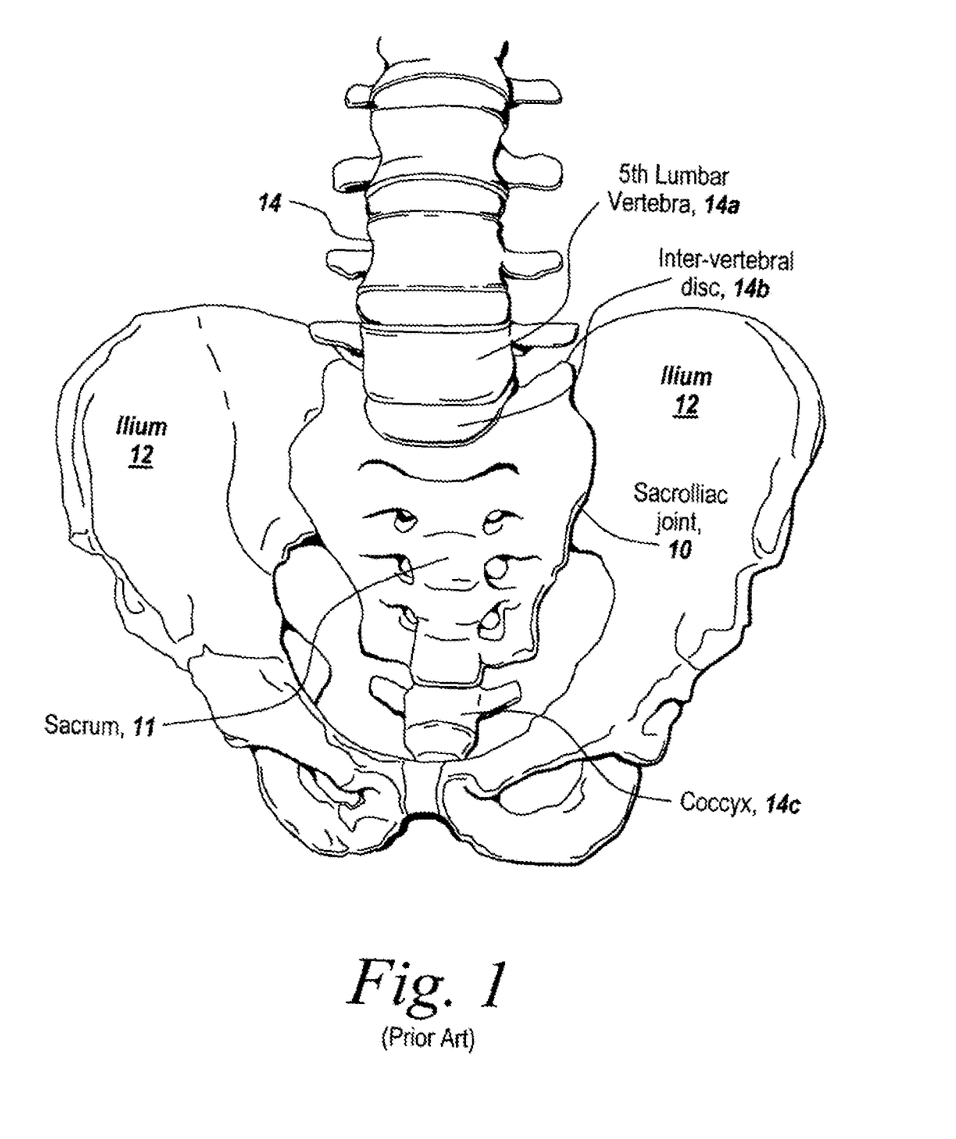
FIG. 1 is a diagrammatic view showing a sacroiliac joint and associated skeletal structure of a human.
Figure 2:
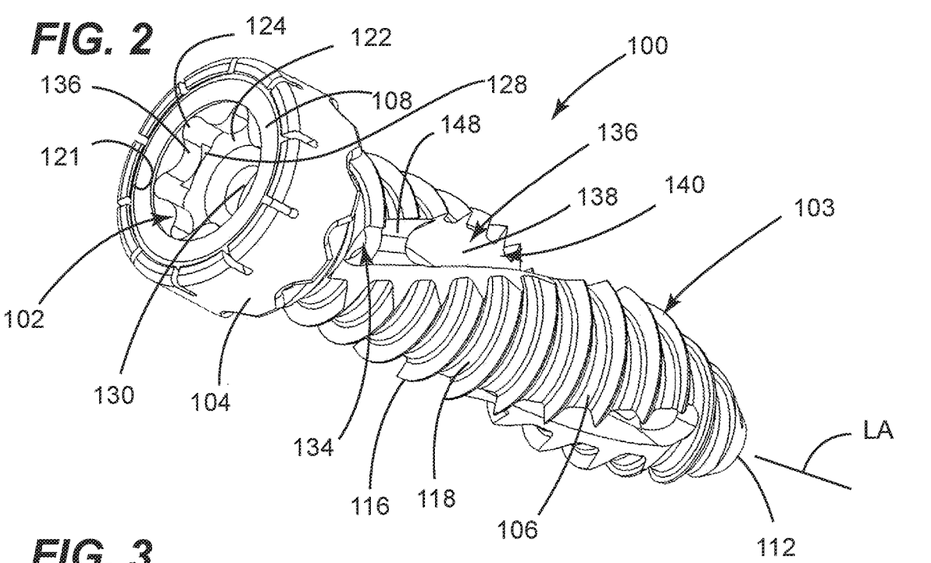
FIG. 2 is a first perspective view showing a bone screw in accordance with an embodiment of the present invention.
Figure 3:
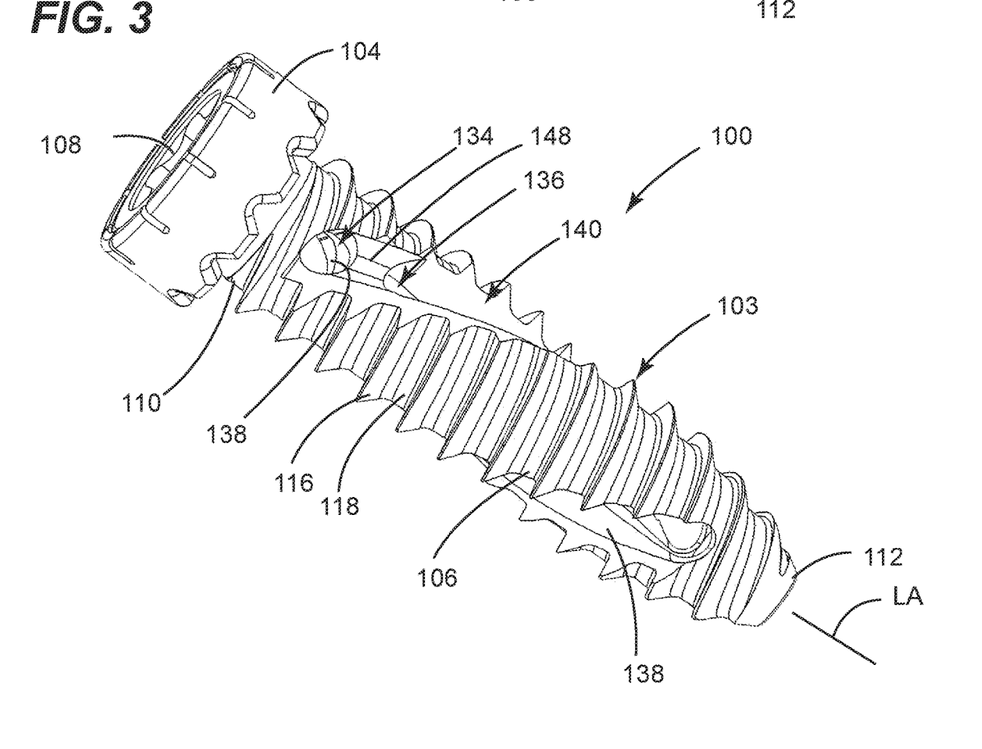
FIG. 3 is a second perspective view of the bone screw shown in FIG. 2.
Figure 4:
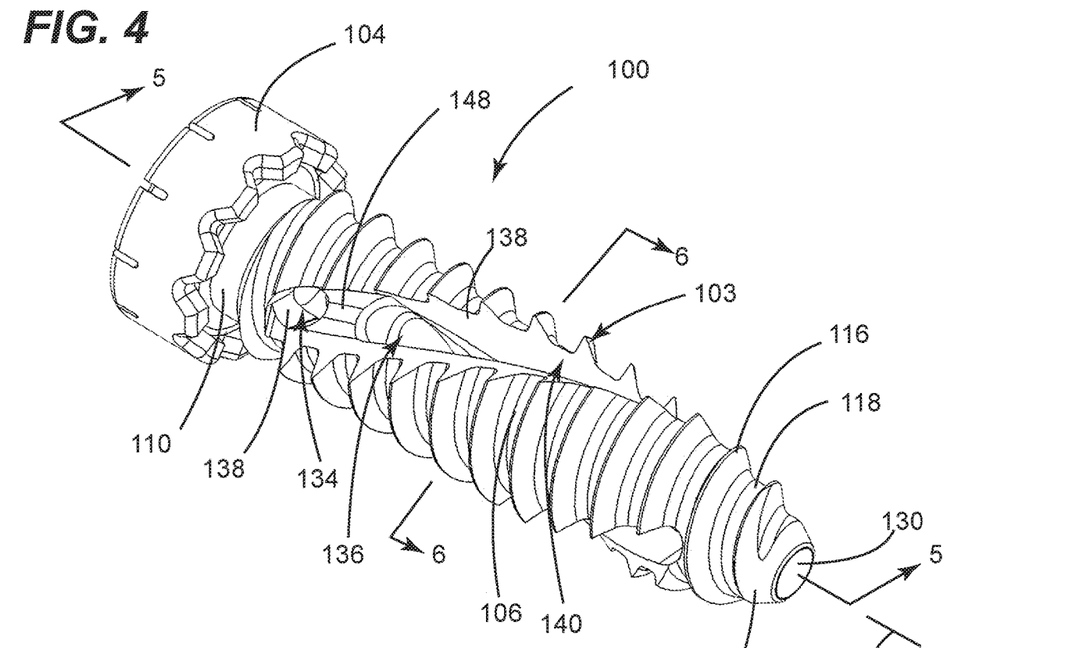
FIG. 4 is a third perspective view of the bone screw shown in FIG. 2.

A specific application for bone screws is sacroiliac joint fusion. As shown in FIG. 1, the sacroiliac (SI) joint 10 is located in the human body between the sacrum 11 and the hip bones 12, known as the ilium. The sacroiliac joint functions to transmit forces from the spine 14, including vertebrae 14a, intervertebral discs 14b and the coccyx 14c, to the lower extremities. The sacroiliac joint 10 is supported by ligaments and muscle. The sacroiliac joint 10 can degenerate over time, requiring a fusion procedure to stabilize the degenerated segment. For example, one condition, degenerative sacroiliitis, results in a narrow joint space with bone spur formation. Iatrogenic (i.e., induced by treatment) procedures, such as iliac bone graft damaging ligaments of the joint and/or previous fusions, can also cause degeneration, requiring sacroiliac joint fusion. Alternatively, infection, ligamentous disruption due to pregnancy, and/or trauma causing fracture dislocation may require a sacroiliac joint fusion procedure to provide sufficient stabilization to allow the patient to achieve a normal lifestyle.

Therefore, a bone screw and tool used therewith for securing bones within a human or animal body in a fixed position with respect to each other and that does not inhibit growth of bone material between such bone pieces is advantageous, desirable and useful.

SUMMARY OF THE DISCLOSURE

Embodiments of the present invention are directed to a bone screw and tool used therewith for securing bones within a human or animal body in a fixed position with respect to each other. Preferably, embodiments of the present invention do not inhibit growth of bone material between such bone pieces and, more preferably, promote the growth of bone material between such bone pieces and around/through the bone screw. A bone screw in accordance with an embodiment of the present invention is further configured with a tool locking structure that is in combination with a torque-applying structure of the bone screw used for placing and extracting the screw. Such tool locking structure advantageously allows the bone screw to be both placed (i.e., rotated in a first direction) and extracted (i.e., rotated in a second direction opposite the first direction) with a common tool (i.e., a placement/extraction tool). The ability to extract (e.g., unscrewed and retracted from a placement location) a bone screw with the same tool used for placing such bone screw is highly beneficial such as due to time savings during a surgical procedure and is advantageous with respect to prior art bone screw configurations that require separate placement and extraction tools.

One configuration of a bone screw useful with a manipulation tool configured in accordance with an embodiment of the present invention comprises a shank portion and a head portion. The shank portion has a proximal end and a distal end. The shank portion includes at least one thread on an exterior surface thereof extending from adjacent the proximal end of the shank portion to adjacent the distal end of the shank portion. The head portion is attached to the shank portion at the proximate end thereof. The head portion includes a tool interface structure therein. The tool interface structure includes a plurality of sidewalls, a floor and a tool lock recess located within at least one of the sidewalls.

Another configuration of a bone screw useful with a manipulation tool configured in accordance with an embodiment of the present invention comprises a main body including a shank portion, a head portion attached to the shank portion, and a cap moveably attached to the head portion. The head portion includes a tool interface structure therein having a closed end portion, an open end portion and a sidewall extending therebetween. A tool lock recess is provided in at least one of the sidewalls of the tool interface structure. The tool interface structure is accessible through an opening within an exterior surface of the cap.

Yet another configuration of a bone screw useful with a manipulation tool configured in accordance with an embodiment of the present invention comprises a shank portion, a head portion, and a cap. The head portion is attached to the shank portion at a proximal end of the shank portion. The cap is moveably attached to the head portion. The shank portion has at least one helically shaped thread on an exterior surface thereof. The thread extends from adjacent the proximal end of the shank portion to adjacent a distal end of the shank portion. The shank portion includes a cannulation passage extending longitudinally therethrough. The cannulation passage defines an interior surface of the shank portion. The shank portion includes at least one bone material aperture therein extending between the exterior surface of the shank portion and the interior surface of the shank portion such that an aperture sidewall is defined between the exterior surface of the shank portion and the interior surface of the shank portion. The head portion includes a tool interface structure therein. The tool interface structure includes a closed end portion, an open end portion and sidewalls extending therebetween. The tool interface structure includes a tool lock enabling feature provided in at least one of the sidewalls thereof. The cannulation passage is exposed at the closed end portion of the tool interface structure. The tool interface structure is accessible through an opening within an exterior surface of the cap.

In another embodiment of the present invention, a screw manipulation tool in accordance with an embodiment of the present invention are shown. The screw manipulation tool is used by a surgeon to place one or more bone screws configured in accordance with an embodiment of the present invention. Advantageously, the screw manipulation tool can be used for placing such a bone screw and/or can be used for extracting (i.e., removing) such a bone screw. A torque-applying structure of the bone screw (i.e., a bone screws configured in accordance with an embodiment of the present invention) is configured to allow the bone screw to be both placed (i.e., rotated in a first direction) and extracted (i.e., rotated in a second direction opposite the first direction) with a common tool. The ability to extract the bone screw with the same tool used for placing it is highly beneficial due to time savings during a surgical procedure and is advantageous with respect to prior art screw configurations that require placement and extraction tools to be differently configured.

These and other objects, embodiments, advantages and/or distinctions of the present invention will become readily apparent upon further review of the following specification, associated drawings and appended claims.

DETAILED DESCRIPTION

Referring now to FIGS. 2-8, various aspects of a bone screw 100 configured in accordance with an embodiment of the present invention are shown. The bone screw 100 can be used for securing bones (i.e., bone pieces including fragments/segments of one or more bones) within a human or animal body in a fixed position with respect to each other. The bone screw 100 is configured in a manner that promotes the growth of bone material between such bone pieces and around/through the bone screw 100 (e.g., via self-harvesting of bone particles). The bone screw 100 is configured with a tool interface structure 102 used for its placement and extraction. The tool interface structure 102 is configured to allow the bone screw 100 to be both placed (i.e., rotated in a first direction) and extracted (i.e., rotated in a second direction opposite the first direction) with a common tool (i.e., a screw manipulation tool). The ability to extract the bone screw 100 with the same tool used for placing it is highly beneficial due to, for example, time savings during a surgical procedure and, thus, is advantageous with respect to prior art screw configurations that require placement and extraction tools to be differently configured.

The bone screw 100 comprises a threaded fastener 103 and a cap 104. The threaded fastener comprises a shank portion 106 and a head portion 108. The shank portion 106 includes a proximal end 110 and a distal end 112. The head portion 108 is attached to the shank portion 106 at the proximal end 110 thereof. As is well known in the art, the shank portion 106 and the head portion 108 are typically concentrically arranged along a common longitudinal axis LA.

The cap 104 is moveably attached to the head portion 108. In preferred embodiments, the head portion 108 is spherically-shaped and the cap 104 includes a mating spherically-shaped receptacle 114 (best shown in FIG. 7) that is seated on the head portion 108. The shank portion 106 has a thread 116 on an exterior surface 118 thereof. The tread 116 extends around the exterior surface 118 of the shank portion 106 in a helical fashion to thereby form a helically-shaped thread. The thread 116 extends from adjacent the proximal end 110 of the shank portion 106 to adjacent a distal end 112 of the shank portion 106.

The tool interface structure 102 is located within the head portion 108. An opening 121 within an exterior surface of the cap 104 enables access to the tool interface structure 102. Advantageously, the tool interface structure 102 being located in the head of the screw as opposed to the shank of the screw enhances its size and resulting strength. Such enhanced size and strength serves to resistance to stripping out during insertion or extraction.

Figure 8:
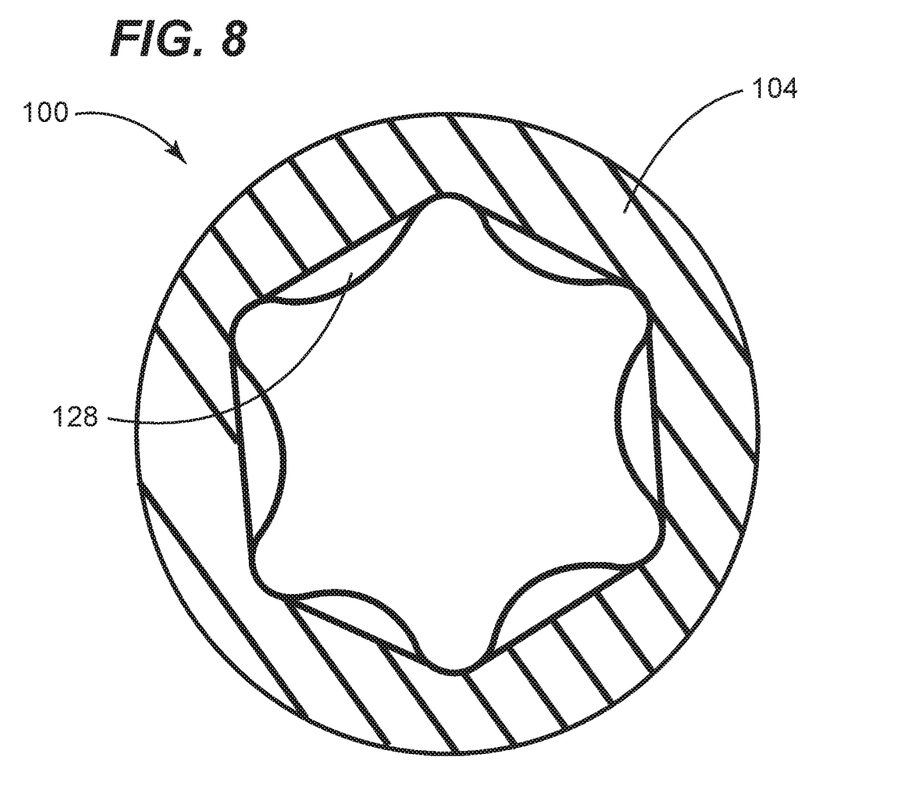
FIG. 8 is a cross-sectional view taken along the line 8-8 in FIG. 7.

The tool interface structure 102 includes a closed end portion 122, an open end portion 124 and sidewalls 126 extending therebetween. The closed end portion 122 can terminate at a floor of the tool interface structure 102 and the open end portion 124 can terminate at a top surface of the head portion 108. The sidewalls 124 can be a plurality of sidewall portions that jointly form a contiguous sidewall. The tool interface structure 102 can include a plurality of tool lock recesses 128 each located within a respective one of the sidewalls 126 or can include a single tool lock recess 128 associated with one of the sidewalls 126. In some embodiments, the tool lock recess 128 is partially defined by the above-mentioned floor of the tool interface structure 102. The sidewalls 126 of the tool interface structure 102 can have the profile commonly referred to as a Phillips drive, a Torx drive, an Allen (i.e., hex) drive, a square drive or the like. As best shown in FIG. 8, each tool lock recess 128 is preferably located within a portion of the sidewall 126 that is inboard of a perimeter region of the tool interface structure 102 as defined by a circle that circumscribes the sidewalls 126.

Each tool lock recesses 128 is an example of a tool lock enabling feature. Such feature enables the bone screw 100 to be fixedly engaged with a mating portion of a screw manipulation tool. In view of the disclosures made herein, a skilled person will appreciate that the tool lock enabling feature can be embodied in a variety of configurations different than a recess as shown.

The shank portion 106 includes a cannulation passage 130 extending longitudinally therethrough. The cannulation passage 130 defines an interior surface 132 of the shank portion 106. The cannulation passage 130 is exposed at the closed end portion 122 of the tool interface structure 102 (e.g., at the floor of the tool interface structure 102), thereby allowing the bone screw 100 to be placed onto and slid along a guide member such as a wire or trocar.

Figure 7:
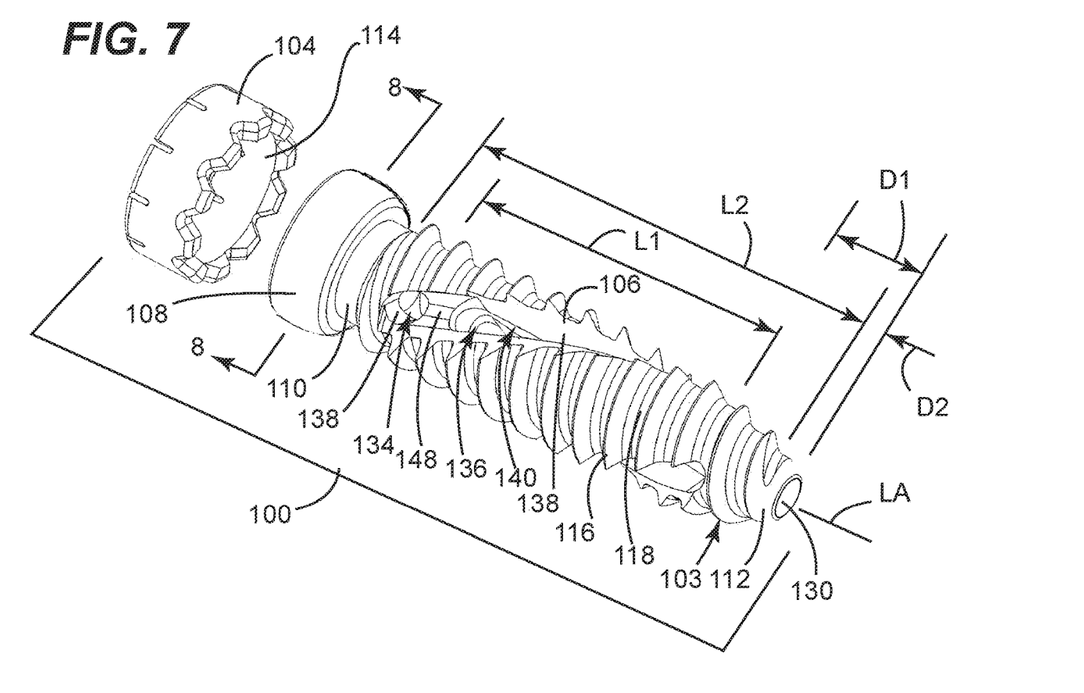
FIG. 7 is an exploded view of the bone screw shown in FIG. 2.

As best shown in FIG. 7, the shank portion 106 includes a plurality of bone material apertures 134, 136 extending between the exterior surface 118 of the shank portion 106 and the interior surface 132 of the shank portion 106 such that an aperture sidewall 138 of each of the apertures 134, 136 is defined between the exterior surface 118 of the shank portion 106 and the interior surface 132 of the shank portion 106. Preferably, the bone material apertures 134, 136 extend through the thread 116 over a first partial length L1 of the shank portion 106 and the thread 116 extends over a second partial length L2 of the shank portion 106. Preferably, the first partial length L1 is shorter than the second partial length L2. For example, each bone material aperture 134, 136 extends through the thread 116 over at least a portion of an entire length of the shank portion 106. Preferably, the second partial length L2 encompasses the first partial length L1. Preferably, the first partial length L1 begins at a first distance D1 from the proximate end 112 of the shank portion 106 and the second partial length L2 begins at a second distance D2 from the proximate end 112 of the shank portion 106. Preferably, a difference between the first distance D1 and the second distance D2 is equal to about a thread pitch distance (i.e., about the distance the screw 100 travels along longitudinal axis LA for one rotation of bone screw 100).

Figure 5:
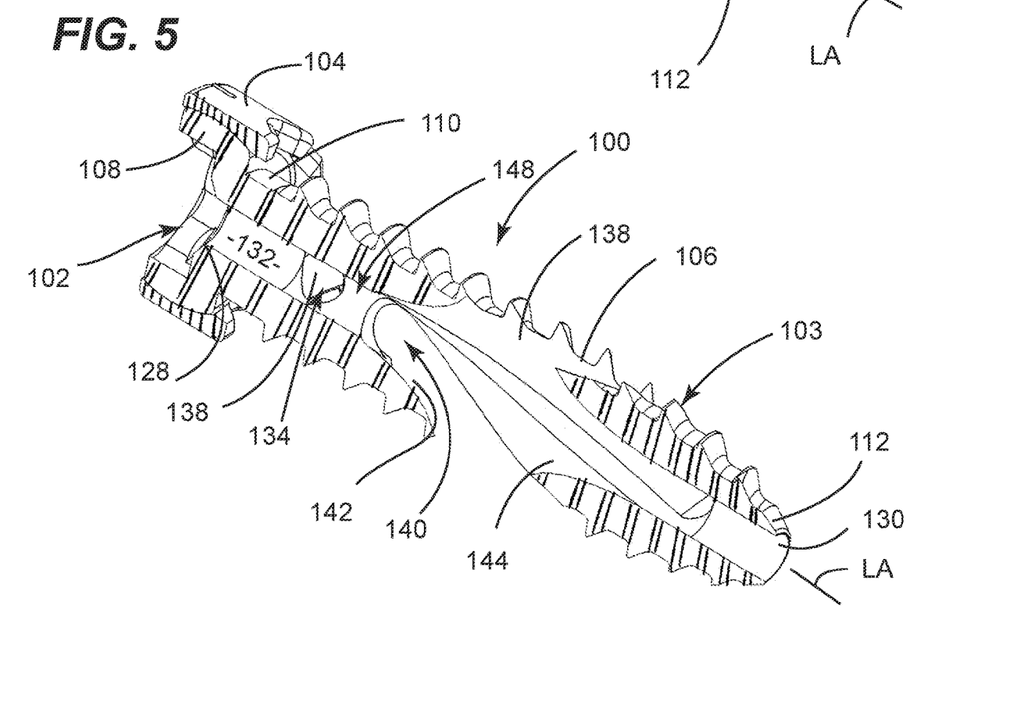
FIG. 5 is a cross-sectional view taken along the line 5-5 in FIG. 4.
Figure 6:
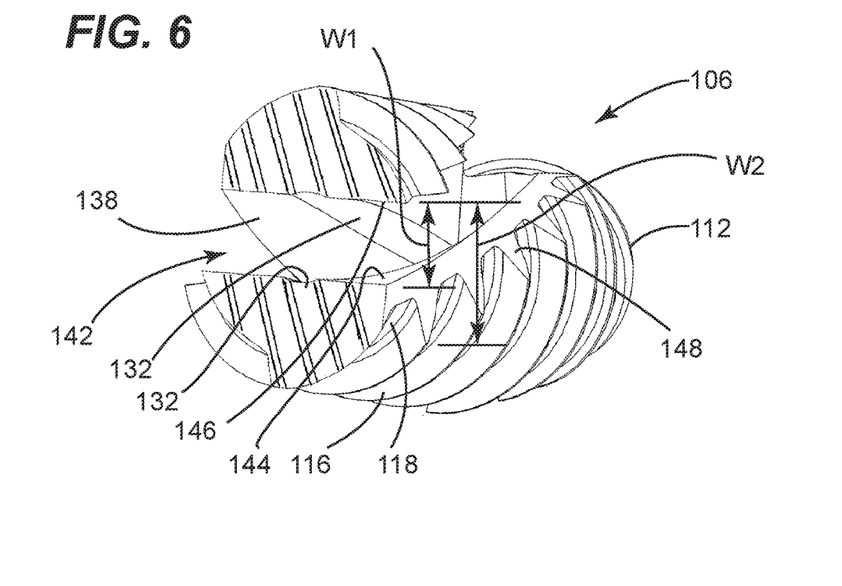
FIG. 6 is a cross-sectional view taken along the line 5-5 in FIG. 4.

Referring to FIGS. 5 and 6, the exterior surface 118 of the shank portion 106 can include a channel 140 therein that extends between a first one of the bone material apertures (e.g., the bone material aperture 134) and a second one of the bone material apertures (e.g., the bone material aperture 136). The channel 140 in combination with the bone material apertures 134, 136 jointly form a contiguous bone material window 142 having opposing side walls 144, 146 and a bridge member 148 attached therebetween. With respect to clockwise rotation of the bone screw 100 (i.e., screw insertion rotation direction), a first one of the opposing side walls (i.e., first opposing side wall 144) of the bone material window 142 defines a leading edge of the bone material window 142 and a second one of the opposing side walls (i.e., second opposing side wall 146) of the bone material window 142 defines a trailing edge of the bone material window 142.

As best shown in FIG. 6, in preferred embodiments, leading edge faces 148 of the thread 116 are reclined with respect to the first opposing side wall 144 (i.e., leading edge) of the bone material window 142. Advantageously, such reclining of the leading edge faces 148 of the thread 116 serves to promote harvesting of bone fragments (e.g., particles) generated from insertion of the bone screw 100 (i.e., self-harvesting functionality). Specifically, relative to a minimum width W1 of the bone material window 142, the reclined leading edge faces 148 of the thread 116 provides an effective width W2 that is greater than the minimum width W1 of the bone material window 142. The benefit of increasing the width of the bone material window 142 is that the width of the bone material window 142 is proportional to a magnitude of thread depth differential created at a bone location that the thread moves past as the bone screw 100 is being placed (i.e., particularly at a portion of the bone screw 100 that is tapered (e.g., nearer to the distal end 112)). In this manner, increasing the effective width W2 of the bone material window 142 promotes/increases harvesting of bone fragments in response to placement of the bone screw 100. In a preferred embodiment, the minimum width of the bone material window 142 (e.g., within the bone material apertures 134, 136) can be equal to about the thread pitch distance and the leading edge faces 148 of the thread 116 are reclined such that a transverse tip-to-tip distance (i.e., about equal to the effective width W2 of the bone material window 142) is at least about 25% greater than the minimum width W1 of the bone material window 142.

In preferred embodiments, the shank portion 106 and the head portion 108 of the threaded fastener 103 are a one-piece component with the cap 104 mounted thereon (e.g., passed over the shank portion 106 and snapped onto the head portion 108). The shank portion 106, the head portion 108 and the cap 104 can be made from a suitable metallic material, suitable polymeric material or a combination thereof. Examples of such suitable metallic materials include stainless steel and titanium. An example of a suitable polymeric material includes PEEK (Polyether ether ketone) polymer. Bone screws configured in accordance with embodiments of the present invention are not unnecessarily limited to being made from any specific material.

Turning now to FIGS. 9-13, various aspects of a screw manipulation tool 200 in accordance with an embodiment of the present invention are shown. The screw manipulation tool 200 is used by a surgeon to place one or more bone screws configured in accordance with an embodiment of the present invention. Advantageously, the screw manipulation tool 200 can be used for placing such a bone screw and/or can be used for extracting (i.e., removing) such a bone screw. As discussed above, the tool interface structure 102 of the bone screw 100 (i.e., a bone screws configured in accordance with an embodiment of the present invention) is configured to allow the bone screw 100 to be both placed (i.e., rotated in a first direction) and extracted (i.e., rotated in a second direction opposite the first direction) with a common tool (e.g., the screw manipulation tool 200). The ability to extract the bone screw 100 with the same tool used for placing it is highly beneficial due to time savings during a surgical procedure and is advantageous with respect to prior art screw configurations that require placement and extraction tools to be differently configured.

The screw manipulation tool 200 includes a main housing 202, a lock member control tube 204, a lock member control mechanism 206, a screw lock member 208 and a torque application drive member 209. The main housing 202 has a proximate end portion 210, a central portion 212 and a distal end portion 214. The proximate end portion 210, the central portion 212 and the distal end portion 214 jointly define a central passage having the lock member control tube 204 rotatably mounted therein with a proximate end portion of the lock member control tube 204 at the proximate end portion 210 of the main housing 202 and a distal end portion of the lock member control tube 204 at the distal end portion 214 of the main housing 202.

Figures 9, 10, 11:
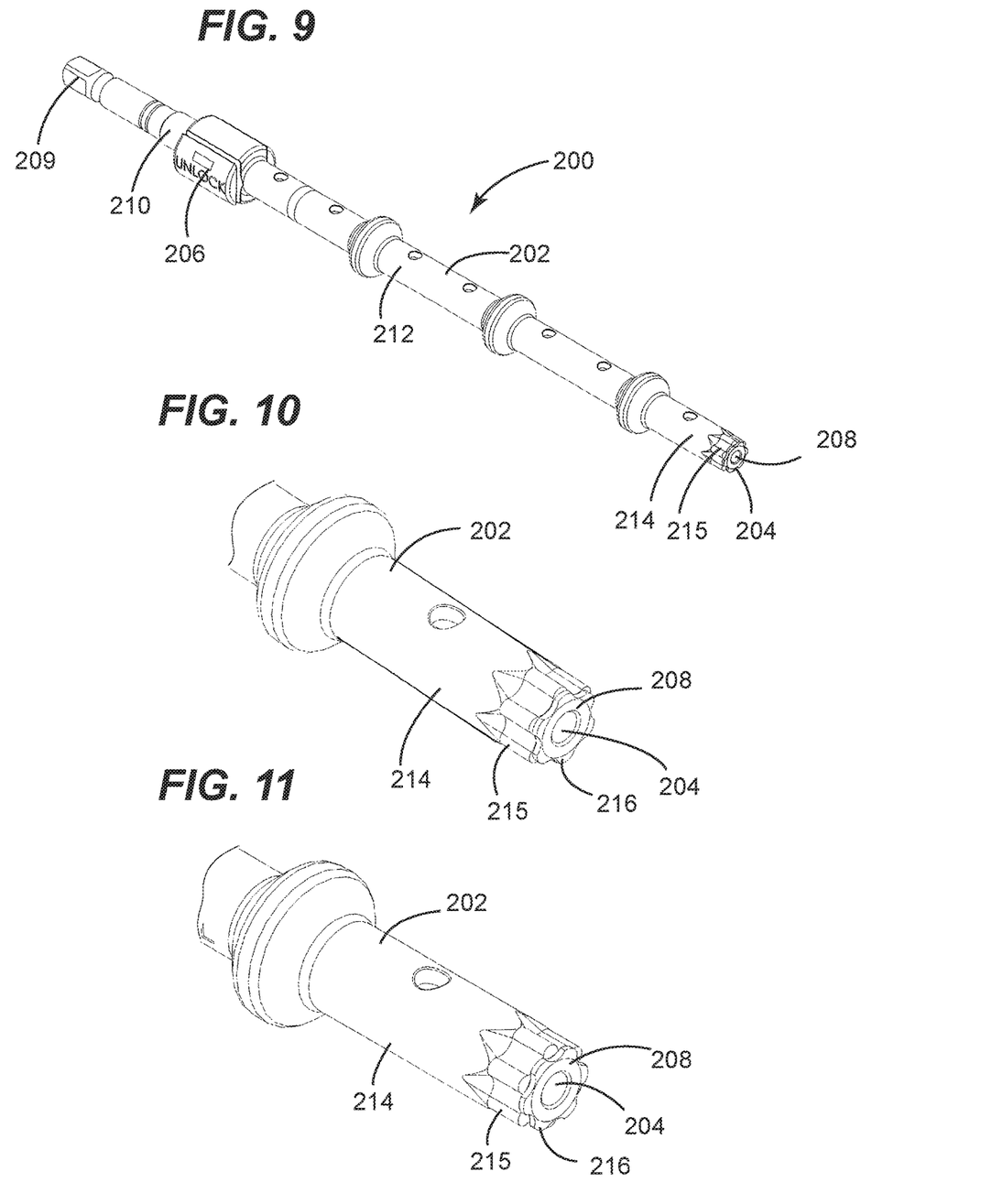
FIG. 9 is a perspective view of a screw manipulation tool in accordance with an embodiment of the present invention.
FIG. 10 is a fragmentary perspective view of a screw engagement end portion of the screw manipulation tool shown in FIG. 9, wherein a screw retention member is in an unlocked orientation
FIG. 11 is a fragmentary perspective view of the screw engagement end portion of the screw manipulation tool shown in FIG. 9, wherein the screw retention member is in a locked orientation.
Figure 13:
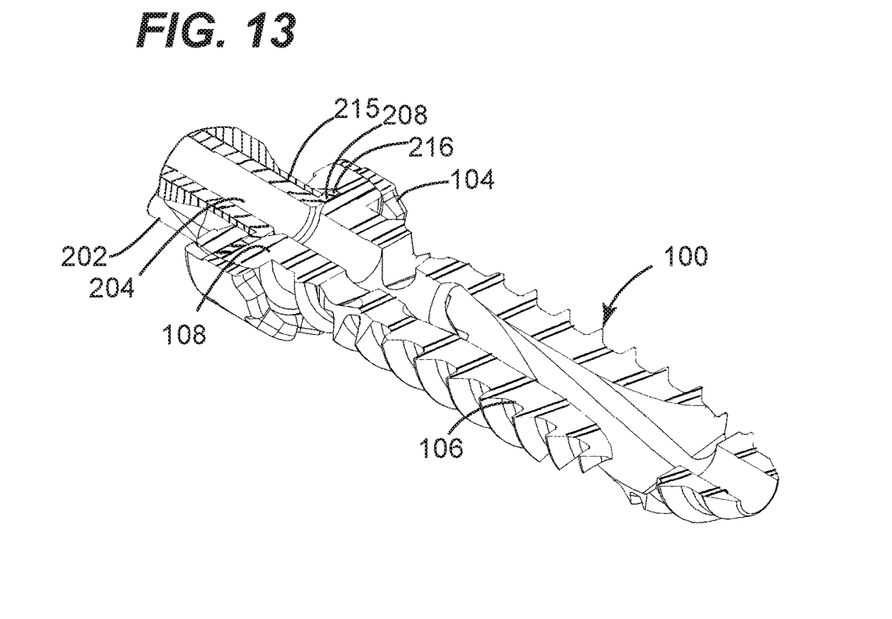
FIG. 13 is a cross-sectional view taken along the line 13-13 in FIG. 12.

As best shown in FIGS. 10, 11 and 13, the distal end portion 214 of the main housing 202 terminates at a tip portion 215 having a cross-sectional profile at its exterior surface that is matingly engageable the tool interface structure 102. To this end, the cross-sectional profile of the tool interface structure 102 can be a profile commonly referred to as a Phillips drive, a Torx drive, an Allen (i.e., hex) drive, a square drive or the like. The screw lock member 208 is attached to the lock member control tube 204 at the distal end portion of the lock member control tube 204 (i.e., adjacent to the distal end portion 214 of the main housing 202). The screw lock member 208 is shaped to allow engagement within a tool lock recess 128 of the bone screw 100. In preferred embodiments, the bone screw 100 includes a plurality of tool lock recesses 128 and the screw lock member 208 includes a plurality of engagement portions 216 each engageable with a respective one of the tool lock recesses 128 through rotation of the lock member control tube 204. Through such engagement of the engagement portion(s) 216 with the tool lock recess(es) 128, the bone screw 100 can be secured onto the distal end portion 214 of the main housing 202 thereby allowing rotation of the bone screw 100 in clockwise and counter-clockwise directions and allowing the bone screw 100 to be moved into a placement location or removed from a placement location.

The lock member control mechanism 206 provides for the screw lock member 208 to be selectively moved (e.g., rotated) between a screw unlock position (FIG. 10) and a screw lock position (FIG. 11) with respect to the tip portion 215 of the main housing 202. In preferred embodiments, the lock member control mechanism 206 is moveably mounted on the main housing 202 and has a portion thereof (not shown) engaged with the lock member control tube 204. Movement of the lock member control mechanism 206 between a first position and a second position causes the screw lock member 208 to correspondingly move between the screw unlock position (i.e., an orientation enabling the engagement portion(s) 216 of the screw lock member 208 to be engaged with the tool lock recess(es) 128 of the bone screw 100) and the screw lock position (i.e., an orientation enabling the engagement portion(s) 216 of the screw lock member 208 to be disengaged with the tool lock recess(es) 128 of the bone screw 100).

Figure 12:
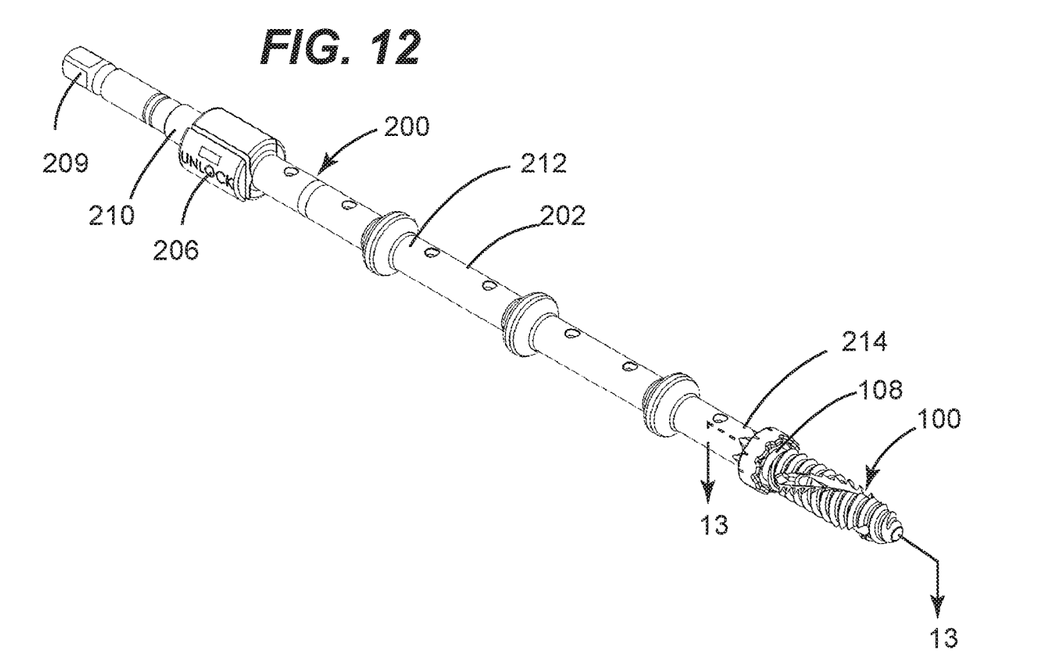
FIG. 12 is a perspective view of the screw manipulation tool shown in FIG. 9, wherein the screw engagement end portion thereof has the bone screw of FIGS. 2-8 engaged therewith.

As shown in FIGS. 9 and 12, the torque application drive member 209 can be attached to the lock member control tube 204 at the proximate end portion of the lock member control tube 204 (i.e., adjacent to the proximate end portion 210 of the main housing 202). The torque application drive member 209 is preferably affixed to the lock member control tube 204 such that rotation of the torque application drive member 209 causes a corresponding rotation of the lock member control tube 204. A skilled person will understand that, in some embodiments, the torque application drive member 209 can be a feature machined into a surface of the lock member control tube 204.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A tool for use with a fastener having one or more tool lock recesses within sidewalls of a tool interface structure that is within a head portion thereof, comprising:
    a fastener engagement structure that is matingly engageable within the tool interface structure of the fastener for inhibiting unrestricted rotation of the fastener relative to the fastener engagement structure while engaged therewith; and
    a screw lock member rotatably attached to the fastener engagement structure, wherein the screw lock member is located adjacent to the fastener engagement structure, wherein the screw lock member includes an engagement portion thereof that is selectively engageable within at least one of the tool lock recesses of the tool interface structure through rotation of the screw lock member relative to the fastener engagement structure for enabling the fastener to be releasably secured to the fastener engagement structure, wherein the screw lock member and the fastener engagement structure each have a common sidewall profile, wherein the screw lock member and the fastener engagement structure are sized for enabling insertion of the screw lock member and the fastener engagement structure into the tool interface structure, wherein the screw lock member is rotatable between a screw unlock position in which a sidewall profile of the screw lock member is aligned with a respective portion of a sidewall profile of the fastener engagement structure and a screw lock position in which at least a portion of the sidewall profile of the screw lock member is misaligned with at least a portion of the sidewall profile of the fastener engagement structure thereby enabling selective alignment and misalignment of the sidewall profile of the screw lock member and the sidewall profile of the fastener engagement structure and wherein at least a portion of the screw lock member becomes located within one or more of the tool lock recesses when the screw lock member is rotated from the screw unlock position to the screw lock position while the fastener engagement structure is matingly engaged within the tool interface structure of the fastener.

2. The tool of claim 1, further comprising:
    an elongated lock member rotation control body coupled at a first end portion thereof to the screw lock member; and
    a lock member control mechanism coupled to a second end portion of the elongated lock member rotation control body, wherein the lock member control mechanism is moveable between a first position in which the elongated lock member rotation control body causes the screw lock member to be in the screw unlock position and a second position in which the elongated lock member rotation control body causes the screw lock member to be in the screw lock position.

3. The tool of claim 2, further comprising:
a housing that includes the fastener engagement structure and a torque application drive member, wherein the torque application drive member enables a rotational torque to be applied to the housing and wherein the elongated lock member rotation control body extends through a central passage of the housing.

4. The tool of claim 3 wherein:
the housing comprises an elongated body having a first end portion including the fastener engagement structure and a second end portion including the torque application drive member; and
a longitudinal axis of the central passage defines a rotational axis of the housing, a rotational axis of the elongated lock member rotation control body and a rotational axis of the screw lock member.

5. A tool for use with a fastener having one or more tool lock recesses within sidewalls of a tool interface structure that is within a head portion thereof, comprising:
a fastener engagement structure that is matingly engageable within the tool interface structure of the fastener for inhibiting unrestricted rotation of the fastener relative to the fastener engagement structure while engaged therewith; and
a screw lock member rotatably attached to the fastener engagement structure, wherein the screw lock member is located adjacent to the fastener engagement structure, wherein the screw lock member includes an engagement portion thereof that is selectively engageable within at least one of the tool lock recesses of the tool interface structure through rotation of the screw lock member relative to the fastener engagement structure for enabling the fastener to be releasably secured to the fastener engagement structure, wherein the screw lock member and the fastener engagement structure each have a common sidewall profile, wherein the screw lock member has a plurality of fastener engagement portions defining the sidewall profile thereof, wherein the sidewall profile of the screw lock member is aligned with the sidewall profile of the fastener engagement structure when the screw lock member is in a screw unlock position and wherein the sidewall of the screw lock member is misaligned with the sidewall profile of the fastener engagement structure when the screw lock member is in a screw lock position.

6. The tool of claim 5, further comprising:
an elongated lock member rotation control body coupled at a first end portion thereof to the screw lock member; and
a lock member control mechanism coupled to a second end portion of the elongated lock member rotation control body, wherein the lock member control mechanism is moveable between a first position in which the elongated lock member rotation control body causes the screw lock member to be in the screw unlock position and a second position in which the elongated lock member rotation control body causes the screw lock member to be in the screw lock position.

7. The tool of claim 6, further comprising:
a housing that includes the fastener engagement structure and a torque application drive member, wherein the torque application drive member enables a rotational torque to be applied to the housing and wherein the elongated lock member rotation control body is an elongated member extending through a central passage of the housing.

8. A tool for use with a fastener having a tool interface structure, comprising:
a housing having a fastener engagement structure, wherein the fastener engagement structure has an exterior surface that is matingly engageable within the tool interface structure of the fastener for inhibiting unrestricted rotation of the fastener relative to the fastener engagement structure of the housing while engaged therewith;
a lock member control mechanism attached to the housing, wherein the lock member control mechanism is moveable between a first position relative to the housing and a second position relative to the housing; and
a screw lock member attached to the lock member control mechanism, wherein the screw lock member abuts an end face of the fastener engagement structure, wherein at least a portion of the screw lock member is moved relative to the fastener engagement structure for being engaged with a lock member receiving portion of the tool interface structure through movement of the lock member control mechanism from the first position to the second position and is moved relative to the fastener engagement structure for being disengaged from the lock member receiving portion of the tool interface structure through movement of the lock member control mechanism from the second position to the first position.

9. The tool of claim 8 wherein:
the screw lock member and the fastener engagement structure each have a common sidewall profile;
the screw lock member and the fastener engagement structure are sized for enabling insertion of the screw lock member and the fastener engagement structure into the tool interface structure; and
the screw lock member is rotatable between a screw unlock position in which the sidewall profile of the screw lock member is aligned with a respective portion of the sidewall profile of the fastener engagement structure and a screw lock position in which at least a portion of the sidewall profile of the screw lock member is misaligned with at least a portion of the sidewall profile of the fastener engagement structure thereby enabling selective alignment and misalignment of the sidewall profile of the screw lock member and the sidewall profile of the fastener engagement structure.

10. The tool of claim 8, further comprising:
a lock member control tube coupled between the screw lock member and the lock member control mechanism for enabling selective movement of the screw lock member about a rotational axis thereof.

11. The tool of claim 10 wherein:
the housing includes a torque application drive member for enabling a rotational torque to be applied to the housing;
the lock member control tube is an elongated member extending through a central passage of the housing; and
the screw lock member is coupled to the lock member control tube through a first end portion thereof.

12. The tool of claim 11 wherein:
the screw lock member and the fastener engagement structure each have a common sidewall profile;
the screw lock member and the fastener engagement structure are sized for enabling insertion of the screw lock member and the fastener engagement structure into the tool interface structure; and the screw lock member is rotatable between a screw unlock position in which the sidewall profile of the screw lock member is aligned with a respective portion of the sidewall profile of the fastener engagement structure and a screw lock position in which at least a portion of the sidewall profile of the screw lock member is misaligned with at least a portion of the sidewall profile of the fastener engagement structure thereby enabling selective alignment and misalignment of the sidewall profile of the screw lock member and the sidewall profile of the fastener engagement structure.

13. The tool of claim 11 wherein:

the housing comprises an elongated body having a first end portion including the fastener engagement structure and a second end portion including the torque application drive member; and a longitudinal axis of the central passage defines a rotational axis of the housing, a rotational axis of the lock member control tube and a rotational axis of the screw lock member.

14. The tool of claim 8 wherein:

the screw lock member and the fastener engagement structure each have a common sidewall profile;

the screw lock member has a plurality of fastener engagement portions defining the sidewall profile thereof;

the sidewall profile of the screw lock member is aligned with the sidewall profile of the fastener engagement structure when the screw lock member is in a screw unlock position; and the sidewall of the screw lock member is misaligned with the sidewall profile of the fastener engagement structure when the screw lock member is in a screw lock position.

15. The tool of claim 14, further comprising:

a lock member control tube coupled between the screw lock member and the lock member control mechanism for enabling selective movement of the screw lock member about a rotational axis thereof.

16. The tool of claim 15 wherein:

the housing comprises the fastener engagement structure and a torque application drive member;

the torque application drive member enables a rotational torque to be applied to the housing;

the lock member control tube is an elongated member extending through a central passage of the housing; and the screw lock member is coupled to the lock member control tube through a first end portion thereof.

17. A tool for use with a fastener having a tool interface structure within in a head portion thereof, comprising:

a housing having a proximate end portion, a central portion and a distal end portion, wherein the proximate end portion, the central portion and the distal end portion jointly define a central passage, and wherein the distal end portion of the housing terminates at a tip portion of the housing and wherein the tip portion has a cross-sectional profile defining an exterior surface that is matingly engageable within the tool interface structure of the fastener for inhibiting unrestricted rotation of the fastener relative to the tip portion of the housing while engaged therewith;

a screw lock member located adjacent to the distal end portion of the housing, wherein the screw lock member is shaped to allow an engagement portion thereof to be engageable within a tool lock recess of the tool interface structure;

a lock member control mechanism attached to the housing, wherein the lock member control mechanism is moveable between a first position relative to the housing and a second position relative to the housing; and a lock member control tube rotatably mounted on the housing within the central passage thereof, wherein the lock member control tube is coupled between the screw lock member and the lock member control mechanism for enabling selective movement of the screw lock member about a rotational axis thereof, wherein the engagement portion of the screw lock member is moved relative to the tip portion of the housing for being engaged with the tool lock recess of the tool interface structure through movement of the lock member control mechanism from the first position to the second position and is moved relative to the tip portion of the housing for being disengaged from the tool lock recess of the tool interface structure through movement of the lock member control mechanism from the second position to the first position.

18. The tool of claim 17 wherein:

the screw lock member and the tip portion of the housing each have a sidewall with a common profile;

the screw lock member has a plurality of fastener engagement portions defining the respective sidewall profile thereof;

the sidewall profile of the screw lock member is aligned with the sidewall profile of the tip portion of the housing when the screw lock member is in a screw unlock position; and the sidewall of the screw lock member is misaligned with the sidewall profile of the tip portion of the housing when the screw lock member is in a screw lock position.

* * * * *